(12) United States Patent
Norman (10) Patent No.: US 7,034,169 B1
(45) Date of Patent: Apr. 25, 2006

(54) VOLATILE METAL β-KETOIMINATE COMPLEXES

(75) Inventor: John Anthony Thomas Norman, Encinitas, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 11/111,455

(22) Filed: Apr. 21, 2005

Related U.S. Application Data (60) Provisional application No. 60/640,338, filed on Dec. 30, 2004.

(51) Int. Cl.
  *C07F 1/08* (2006.01)
  *C23C 16/00* (2006.01)
  *B32B 15/04* (2006.01)

(52) U.S. Cl. ............... 556/10; 556/12; 556/37; 556/113; 427/248.1; 428/457; 428/697

(58) Field of Classification Search ............ 556/10, 556/12, 37, 113; 427/248.1; 428/457, 697
  See application file for complete search history.

(56) References Cited

U.S. PATENT DOCUMENTS

| | | | |
|---|---|---|---|
| 5,098,516 | A | 3/1992 | Norman et al. |
| 6,372,928 | B1 * | 4/2002 | Kawaguchi et al. ......... 556/10 |
| 6,538,147 | B1 | 3/2003 | Choi |
| 6,552,209 | B1 | 4/2003 | Lei et al. |
| 6,620,956 | B1 * | 9/2003 | Chen et al. ............... 556/110 |
| 6,818,783 | B1 | 11/2004 | Norman et al. |
| 6,822,107 | B1 * | 11/2004 | Baum et al. .............. 556/113 |
| 6,869,876 | B1 | 3/2005 | Norman et al. |
| 2003/0012876 | A1 * | 1/2003 | Min et al. ............... 427/248.1 |
| 2003/0129308 | A1 | 7/2003 | Chen et al. |
| 2004/0247905 | A1 | 12/2004 | Bradley et al. |

FOREIGN PATENT DOCUMENTS

| | | | |
|---|---|---|---|
| GB | 1 263 720 | * | 2/1972 |
| JP | 06145986 | | 11/1992 |
| WO | WO 200166347 A1 | | 3/2000 |
| WO | WO 200168580 A1 | | 3/2000 |

OTHER PUBLICATIONS

Martensson, et al., "Atomic Layer Epitaxy of Copper", J. Electrochem. Soc., vol. 145, No.8, Aug. 1998, pp. 2926-2931.
Awaya, et al., "Double-Level Copper Interconnections Using Selective Cooper CVD", Journal of Electronic Materials, vol. 21, No. 10, 1992, pp. 959-964.
Fine, et al., "Organometallic Chemical Vapor Deposition of Copper From A New Organometallic Precursor", Mat. Res. Soc. Symp. Proc., vol. 204, 1991, pp. 415-420.
Beach, et al., "Low-Temperature Chemical Vapor Deposition of High-Purity Copper from an Organometallic Source", Chem. Mater. 1990, 2, 216-219.
Kroger, et al., "Properties of Copper Films Prepared by Chemical Vapor Deposition for Advanced Metallization of Microelectronic Devices", Journal of the Electrochemical Society, 146 (9) 3248-3254 (1999).
Shin, et al., "Synthesis of Volatile, Fluorinated B-Ketoiminato Copper(i) Complexes", J. Chem. Soc., Chem. Commun., 1992, pp. 217-219.
CA Selects: Chemical Vapor Deposition (CVD), Issue 7, 1996, p. 16.

* cited by examiner

*Primary Examiner*—Porfirio Nazario-Gonzalez
(74) *Attorney, Agent, or Firm*—Geoffrey L. Chase (57) ABSTRACT

Metal complexes, containing copper, silver, gold, cobalt, ruthenium, rhodium, platinum, palladium, nickel, osmium, and/or indium, and methods for making and using same are described herein. In certain embodiments, the metal complexes described herein may be used as precursors to deposit metal or metal-containing films on a substrate through, for example, atomic layer deposition or chemical vapor deposition conditions.

15 Claims, 2 Drawing Sheets

VOLATILE METAL β-KETOIMINATE COMPLEXES

CROSS-REFERENCE TO RELATED APPLICATIONS

This application claims the benefit of U.S. Provisional Application No. 60/640,338, filed 30 Dec. 2004.

BACKGROUND OF THE INVENTION

The semiconductor industry uses metal-containing interconnects, such as copper (Cu), in electronic devices such as, for example, state of the art microprocessors. The metal-containing interconnects, which may be embedded fine metal lines, form the three dimensional grid upon which millions of transistors at the heart of the microprocessor can communicate and perform complex calculations. In these and other applications, copper or alloys thereof may be chosen over other metals such as, for example, aluminum because copper is a superior electrical conductor, thereby providing higher speed interconnections of greater current carrying capability.

Interconnect pathways within electronic devices are typically prepared by the damascene process, whereby photolithographically patterned and etched trenches and vias in the dielectric insulator are coated with a conformal thin layer of a diffusion barrier material. A diffusion barrier layer is typically used in conjunction with a metal or copper layer to prevent detrimental effects caused by the interaction or diffusion of the metal or copper layer with other portions of the integrated circuit. Exemplary barrier materials include, but are not limited to, titanium, tantalum, tungsten, chromium, molybdenum, zirconium, ruthenium, vanadium, and/or platinum as well as carbides, nitrides, carbonitrides, silicon carbides, silicon nitrides, and silicon carbonitrides of these materials and alloys comprising same. In certain processes, such as when, for example, the interconnect comprises copper, the diffusion barrier layer may be coated with a thin 'seed' or 'strike' layer of copper, prior to completely filling in the features with pure copper. In still other cases, the seed layer of copper may be replaced by—or used in addition to—an analogous cobalt or similar conducting thin film 'glue' layer. Excess copper may then be removed by the process of chemical mechanical polishing. Since the smallest features to be filled can be less than 0.2 microns wide and over 1 micron deep, it is preferable that the copper seed layer, copper glue layer and/or the diffusion barrier layers be deposited using metallization techniques that are capable of evenly filling these features, without leaving any voids, which could lead to electrical failures in the finished product.

Numerous methods such as ionized metal plasma (IMP), physical vapor deposition (PVD), chemical vapor deposition (CVD), atomic layer deposition (ALD), plasma-assisted chemical vapor deposition (PACVD), plasma-enhanced chemical vapor deposition (PECVD), electroplating, and electroless plating have been used to deposit metal-containing layers such as the metallization, diffusion barrier, and/or other layers. Among them, CVD and ALD methods using one or more organometallic precursors may be the most promising methods because these methods provide excellent step coverage for high aspect ratio structures and good via filling characteristics. In a typical CVD process, a vapor of a volatile organometallic precursor containing the desired metal is introduced to a substrate surface whereupon a chemical reaction occurs in which a thin film containing the metal as a compound or as a pure element is deposited on the substrate. Since the metal is typically delivered in a vapor form as a volatile precursor, it can access both vertical and horizontal surfaces to provide an evenly distributed thin film. In a typical ALD process, a volatile organometallic precursor is alternately pulsed into a reactor with a reagent gas such that self-limiting alternating monolayers of precursor/reagent are deposited on the substrate wherein the monolayers react together to form a metal film or a metal-containing film which is subsequently reduced to metal or used as deposited. For example, if a copper organometallic precursor was reacted with a suitable oxidant in an ALD process, the resulting cuprous oxide or cupric oxide monolayer or multilayer could be used for semiconductor applications or reduced to copper metal.

For copper thin films, some of the same precursors suitable for CVD and other depositions may also be suitable as ALD precursors. In certain applications, it may be preferable that the precursor be highly volatile, deposit copper films that are substantially pure (i.e., have a purity of about 95% or about 99% or greater copper), and/or minimize the introduction of potentially contaminating species into the reaction chamber or onto the diffusion barrier or other underlying surfaces. Further, in these applications, it may be preferable that the copper film exhibits good adhesion to the diffusion barrier layer because poor adhesion may lead to, inter alia, delamination of the copper film during chemical mechanical polishing.

Several organometallic precursors have been developed to deposit low electrical resistivity copper films by the aforementioned processes, particularly CVD or ALD processes. Two of often-used families of copper organometallic precursors that have been studied extensively are the Cu(I) and Cu(II) precursors. One commonly used Cu(I) precursor is a precursor having the formula "Cu(I)(hfac)(W)" precursor where "hfac" represents the 1,1,1,5,5,5-hexafluoro-2,4-pentanedionate anion and (W) represents a neutral stabilizing ligand, such as, for example, an olefin, an alkyne, or a trialkylphosphine. One particular example of a Cu(I) precursor having the above formula is 1,1,1,5,5,5-hexafluoro-2,4-pentanedionato-copper (I) trimethylvinylsilane (hereinafter Cu(hfac)(tmvs)), which is sold under the trademark CUPRASELECT™ by Air Products and Chemicals, Inc. of Allentown, Pa., the assignee of the present application. These Cu(I) precursors can deposit films via a disproportionation reaction whereby two molecules of the precursor react on a heated substrate surface to provide copper metal, two molecules of free ligand (W), and the volatile by-product $Cu^{(+2)}(hfac)_2$. Equation (1) provides an example of a disproportionation reaction:

$$2Cu^{(+1)}(hfac)W \rightarrow Cu+Cu^{(+2)}(hfac)_2+2W \quad (1)$$

In CVD depositions, the disproportionation reaction illustrated in Equation (1) is typically run at a temperature of around 200° C.; however, other temperatures may be used depending upon the deposition process. As Equation (1) illustrates, the $Cu^{(+2)}(hfac)_2$ constitutes a byproduct from the reaction and may need to be removed from the reaction chamber.

Yet another type of Cu(I) precursor is a precursor having the formula "(X)Cu(Y)". In these particular Cu(I) precursors, "X" is an organic anion and "Y" is a neutral stabilizing ligand, such as, for example, trialkyphosphine. An example of such a precursor is $CpCuPEt_3$, where Cp is cyclopentadienyl and $PEt_3$ is triethylphoshine. Under typical CVD conditions, two of these precursor molecules may react on a wafer surface, whereby the two stabilizing trialkyphosphine Y ligands become disassociated from the copper centers, the two (X) ligands become coupled together, and the copper (I) centers are reduced to copper metal. The overall reaction is shown below in Equation (2).

$$2(X)Cu(Y) \rightarrow 2Cu + (X-X) + 2(Y) \quad (2)$$

However, in certain instances, this type of chemistry may present problems because the released trialkylphosphine ligands may contaminate the reaction chamber and act as undesired N-type silicon dopants.

As mentioned previously, yet another type of precursor used to deposit copper-containing films is Cu(II) precursors. Unlike the Cu(I) precursors, the Cu(II) precursors require the use of an external reducing agent such as, for example, hydrogen or alcohol to deposit copper films that are largely free of impurities. An example of a typical Cu(II) precursor has the chemical formula Cu(II)(Z)$_2$ wherein (Z) is an organic anion. Examples of this type of precursor include, but are not limited to, Cu(II)bis(β-diketonates), Cu(II) bis (β-diimine), and Cu(II) bis(β-ketoimine) complexes. Equation (3) provides an illustration of a deposition reaction wherein hydrogen is used as the reducing agent.

$$Cu(II)(Z)_2 + H_2 \rightarrow Cu + 2ZH \quad (3)$$

The Cu(II) precursors are typically solids and the temperatures required for film deposition are typically above 200° C.

While copper precursors are widely used as interconnects, other metals or alloys are used as thin films in electronic devices. Examples of such metals include silver (Ag), gold (Au), cobalt (Co), ruthenium (Ru), rhodium (Rh), platinum (Pt), palladium (Pd), nickel (Ni), osmium (Os), indium (In), and alloys thereof.

BRIEF SUMMARY OF THE INVENTION

Metal-containing complexes, and methods for making and using same, such as for example as a precursor in a deposition process, are described herein. In one aspect, there is provided a complex represented by the following formulas (I) or (II):

wherein M is a metal selected from Cu, Au, Ag, Co, Ru, Rh, Pt, In, Pd, Ni, Os, and mixtures thereof;

wherein R$^1$, R$^2$, R$^3$, and R$^4$ are each independently a hydrogen atom; an alkyl having a formula C$_n$H$_{2n+1}$ wherein n is a number ranging from 1 to 20; a fluoroalkyl having a formula C$_n$H$_x$F$_y$ wherein the product of (x+y) equals the product of (2n+1) and n is a number ranging from 1 to 20; an alkylsilane having a formula (R$^5$)$_3$Si wherein R$^5$ is each independently an alkyl, a fluoralkyl, an amide, or an alkoxy comprising from 1 to 20 carbon atoms; an aryl comprising from 6 to 18 carbon atoms; an alkyl-substituted aryl comprising from 6 to 18 carbon atoms; a fluoroalky-substituted aryl comprising from 6 to 18 carbon atoms; a fluoroaryl comprising from 6 to 18 carbon atoms; an alkyl-substituted fluoroaryl comprising from 6 to 18 carbon atoms; a fluoroalkyl-substituted fluoroaryl comprising from 6 to 18 carbon atoms; an ether having a formula (CH$_2$)$_n$O(C$_m$H$_{2m+1}$) where n is a number ranging from 1 to 20 and m is a number ranging from 1 to 20; an alkoxy comprising from 1 to 20 carbon atoms; an amide group comprising from 1 to 20 carbon atoms; a halogen atom; and a nitro group NO$_2$;

wherein L is a ligand selected from carbon monoxide; an alkylnitrile comprising from 2 to 20 carbon atoms; a silylnitrile having a formula (R$^6$)$_3$SiCN wherein R$^6$ is each independently an alkyl comprising from 1 to 20 carbon atoms; an alkyne comprising from 1 to 20 carbon atoms; a silylalkyne having a formula (R$^7$)$_3$SiCCR$^8$ wherein R$^7$ is each independently an alkyl, an amide, or an alkoxy comprising from 1 to 20 carbon atoms and R$^8$ is each independently a hydrogen atom, an alkoxy, or an alkyl comprising from 1 to 20 carbon atoms; a bis(silyl)alkyne having a formula (R$^9$)$_3$SiCCSi (R$^9$)$_3$ wherein R$^9$ is each independently an alkyl, an amide or an alkoxy comprising from 1 to 20 carbon atoms; an alkene comprising from 1 to 20 carbon atoms; a diene comprising from 1 to 20 carbon atoms; a triene comprising from 1 to 20 carbon atoms; a silylalkene having a formula (R$^{10}$)$_3$SiC(R$^{17}$)C(R$^{17}$)$_2$ wherein R$^{10}$ is each independently an alkyl, an alkoxy, or an amide comprising from 1 to 20 carbon atoms and R$^{17}$ is independently a hydrogen atom or an alkyl group comprising from 1 to 20 carbon atoms; a bis(silyl) alkene having a formula (R$^{11}$)$_3$SiCR$^{17}$CR$^{17}$Si(R$^{11}$)$_3$ wherein R$^{11}$ is each independently an alkyl comprising from 1 to 20 carbon atoms, an alkoxy, or an amide comprising from 1 to 20 carbon atoms and R$^{17}$ is independently a hydrogen atom or an alkyl group comprising from 1 to 20 carbon atoms; an allene comprising from 3 to 20 carbon atoms; an allene having a formula (R$^{12}$)$_2$CCC(R$^{12}$)$_2$ where R$^{12}$ is each independently a hydrogen atom, an alkyl, an alkyl silane, an alkoxysilane, or an amidosilane having a formula (R$^{13}$) $_3$Si wherein R$^{13}$ is each independently an alkyl, alkoxy, or an amide comprising from 1 to 20 carbon atoms; an alkylisocyanide comprising from 1 to 20 carbon atoms; a silylisocyanide having a formula (R$^{14}$)$_3$SiNC wherein R$^{14}$ is each independently an alkyl comprising from 1 to 20 carbon atoms; an allyl comprising from 1 to 20 carbon atoms; an allylsilane having a formula (R$_{15}$)$_3$SiC (R$^{17}$)$_2$R$^{17}$C(R$^{17}$)$_2$ where R$^{15}$ is an alkyl, an alkoxy, or an amide comprising from 1 to 20 carbon atoms and R$^{17}$ is independently a hydrogen atom or an alkyl group having from 1 to 20 carbon atoms; and a bis(silyl)allyl having a formula (R$^{16}$)$_3$SiC(R$^{17}$)$_2$CR$^{17}$CR$^{17}$Si(R$^{16}$)$_3$ where R$^{16}$ comprises from 1 to 20 carbon atoms and R$^{17}$ is independently a hydrogen atom or an alkyl group having from 1 to 20 carbon atoms; and wherein an organometallic bond between M and L is selected from 2 single bonds and 1 single bond.

In another aspect, there is provided a process for depositing a metal film comprising copper on a substrate comprising: contacting the substrate with a complex having the above formula (I) or (II) wherein the contacting is conducted at conditions sufficient for the complex to react and form the film.

In a further aspect, there is provided an electronic device comprising a film comprising metal wherein the film is deposited using a complex having the above formula (I) or (II).

In yet another aspect, there is provided a method of making a complex having the above formula (I) or (II) comprising: reacting a primary amine with a β-diketone compound to form a β-ketoimine intermediate product; and deprotonating the β-ketoimine intermediate product using a base in the presence of a metal source and the ligand (L) to form the complex having the formula (I) or (II).

DETAILED DESCRIPTION OF THE INVENTION

Metal-containing complexes and methods for making and using same are described herein. The metal complexes may, in certain embodiments, react via a disproportionation reaction. In alternative embodiments, the metal complexes can be reacted in the presence of a reducing agent. The metal complexes may be used, for example, as a precursor to deposit metal or metal-containing films via a variety of deposition processes, including CVD or ALD processes. In these processes, the complexes can be used to grow thin metal films by CVD or ALD by reacting the complexes with a suitable reagent. For example, in one embodiment, reaction of a copper-containing complex with a halogen source reagent may form a thin film of copper halide, whereas in another embodiment, reaction with a suitable oxidant may yield a copper oxide film. The metal films could be used as-deposited or, alternatively, could be reduced to metal using a suitable reducing agent.

The metal containing complexes described herein have the following formula (I) or (II):

(I)

In the above formulas, M is a metal selected from Cu, Au, Ag, Co, Ru, Rh, Pt, In, Pd, Ni, Os, and mixtures thereof. In certain embodiments, M is copper. In the above formulas, substituents $R^1$, $R^2$, $R^3$, and $R^4$ can each independently be a hydrogen atom; an alkyl having a formula $C_nH_{2n+1}$ wherein n is a number ranging from 1 to 20; a fluoroalkyl having a formula $C_nH_xF_y$ wherein the product of (x+y) equals the product of (2n+1) and n is a number ranging from 1 to 20; an alkylsilane having a formula $(R^5)_3Si$ wherein $R^5$ is each independently an alkyl, a fluoralkyl, an amide, or an alkoxy comprising from 1 to 20 carbon atoms; an aryl comprising from 6 to 18 carbon atoms; an alkyl-substituted aryl comprising from 6 to 18 carbon atoms; a fluoroalky-substituted aryl comprising from 6 to 18 carbon atoms; a fluoroaryl comprising from 6 to 18 carbon atoms; an alkyl-substituted fluoroaryl comprising from 6 to 18 carbon atoms; a fluoroalkyl-substituted fluoroaryl comprising from 6 to 18 carbon atoms; an ether having a formula $(CH_2)_nO(C_mH_{2m+1})$ where n is a number ranging from 1 to 20 and m is a number ranging from 1 to 20; an alkoxy comprising from 1 to 20 carbon atoms; an amide group comprising from 1 to 20 carbon atoms; a halogen atom; or a nitro group $NO_2$. In formula (I), ligand L can be selected from carbon monoxide; an alkylnitrile comprising from 2 to 20 carbon atoms; a silylnitrile having a formula $(R^6)_3SiCN$ wherein $R^6$ is each independently an alkyl comprising from 1 to 20 carbon atoms; an alkyne comprising from 1 to 20 carbon atoms; a silylalkyne having a formula $(R^7)_3SiCCR^8$ wherein $R^7$ is each independently an alkyl, an amide, or an alkoxy comprising from 1 to 20 carbon atoms and $R^8$ is each independently a hydrogen atom, an alkoxy, or an alkyl comprising from 1 to 20 carbon atoms; a bis(silyl)alkyne having a formula $(R^9)_3SiCCSi(R^9)_3$ wherein $R^9$ is each independently an alkyl, an amide or an alkoxy comprising from 1 to 20 carbon atoms; an alkene comprising from 1 to 20 carbon atoms; a diene comprising from 1 to 20 carbon atoms; a triene comprising from 1 to 20 carbon atoms; a silylalkene having a formula $(R^{10})_3SiC(R^{17})C(R^{17})_2$ wherein $R^{10}$ is each independently an alkyl, an alkoxy, or an amide comprising from 1 to 20 carbon atoms and $R^{17}$ is independently a hydrogen atom or an alkyl group comprising from 1 to 20 carbon atoms; a bis(silyl)alkene having a formula $(R_{11})_3SiCR^{17}CR^{17}Si(R^{11})_3$ wherein $R^{11}$ is each independently an alkyl comprising from 1 to 20 carbon atoms, an alkoxy, or an amide comprising from 1 to 20 carbon atoms and $R^{17}$ is independently a hydrogen atom or an alkyl group comprising from 1 to 20 carbon atoms; an allene comprising from 3 to 20 carbon atoms; a allene having a formula $(R_{12})_2CCC(R^{12})_2$ where $R^{12}$ is each independently a hydrogen atom, an alkyl, an alkyl silane, an alkoxysilane, or an amidosilane having a formula $(R^{13})_3Si$ wherein $R^{13}$ is each independently an alkyl, alkoxy, or an amide comprising from 1 to 20 carbon atoms; an alkylisocyanide comprising from 1 to 20 carbon atoms; a silylisocyanide having a formula $(R^{14})_3SiNC$ wherein $R^{14}$ is each independently an alkyl comprising from 1 to 20 carbon atoms; an allyl comprising from 1 to 20 carbon atoms; an allylsilane having a formula $(R^{15})_3SiC(R^{17})_2R^{17}C(R^{17})_2$ where $R^{15}$ is an alkyl, an alkoxy, or an amide comprising from 1 to 20 carbon atoms and $R^{17}$ is independently a hydrogen atom or an alkyl group having from 1 to 20 carbon atoms; and a bis(silyl)allyl having a formula $(R^{16})_3SiC(R^{17})_2CR^{17}CR^{17}Si(R^{16})_3$ where $R^{16}$ comprises from 1 to 20 carbon atoms and $R^{17}$ is independently a hydrogen atom or an alkyl group having from 1 to 20 carbon atoms.

The term "alkyl" as used herein includes straight chain, branched, or cyclic alkyl groups, comprising from 1 to 20 carbon atoms or from 1 to 10 carbon atoms. Exemplary alkyl groups include methyl, ethyl, n-propyl, isopropyl, n-butyl, isobutyl, sec-butyl, tertbutyl, tert-amyl, n-pentyl, n-hexyl, cyclopentyl, and cyclohexyl. The term "alkyl" also applies to alkyl moieties contained in other groups such as haloalkyl, alkylaryl, or arylalkyl. The term "aryl" as used herein comprises 6 to 18 member carbon rings having aromatic character. Exemplary aryl groups include phenyl and napthyl groups. The term "alkyl-substituted aryl" applies to aryl moieties that are alkyl substituted. Exemplary alkyl-substituted aryl groups include tolyl and xylyl groups. The terms "halo" and "halogen" include fluorine, chlorine, bromine, or iodine. The term "fluoroalkyl" applies to alkyl moieties wherein one or more of its hydrogen atoms are replaced by a fluorine halogen atom, may be partially or fully fluorinated, and includes straight chain, branched or cyclic fluorinated alkyl groups comprising from 1 to 20 carbon atoms or from 1 to 10 carbon atoms. Exemplary fluoroalkyl groups include $-CF_3$, $-CF_2CF_3$, $-CH_2CF_3$, $-CF_2CFH_2$, or $-CH_2CF_2CF_3$. In certain embodiments, some of the groups discussed herein may be substituted with one or more other elements such as, for example, a halogen atom or other heteroatoms such as O, N, Si, or S.

In certain embodiments, the metal complexes described herein may contain fluorine. In these embodiments, any one or all of substituents $R^1$, $R^2$, $R^3$, and $R^4$ may contain fluorine such as, for example, a fluoroalkyl, a fluoroalkyl-substituted aryl, a fluoroaryl, an alkyl-substituted fluoroalkyl, or a fluoroalkyl-substituted fluoroaryl group. In alternative embodiments, the metal complexes described herein do not contain fluorine.

In certain embodiments, any one or all of substituents $R^1$, $R^2$, $R^3$ and $R^4$ can be independently connected to form cyclic structures. In certain embodiments, $R^3$ and $R^4$ and/or $R^1$ and $R^2$ can be independently linked to form cyclic structures.

In certain embodiments, the metal complex has the formula (II). In these embodiments, ligand L may be for example, an alkyne or diene, and is coordinated to two metal-containing ketoimine units as shown below in formula (II). In these embodiments, metal atom M may be the same, or alternatively different, metal atoms. In the later embodiments, this may allow for the deposition of mixed metal films.

(II)

In one embodiment, ligand L in formula (I) or (II) may be an alkylnitrile such as, but not limited to, MeCN or Me$_3$CCN. In an alternative embodiment, ligand L in formula (I) or (II) may be a silylnitrile such as but not limited to Me$_3$SiCN. In a further embodiment, ligand L in formula (I) or (II) may be a alkyne such as but not limited to MeCCMe or MeCCH. In another embodiment, ligand L in formula (I) or (II) may be a alkene such as but not limited to Me$_3$CCHCH$_2$ or Me(CH$_2$)$_2$CHCH$_2$. In yet another embodiment, ligand L in formula (I) or (II) may be a silylalkene having the formula $(R^{10})_3SiCR^{17}C(R^{17})_2$ or a bis(silyl)alkene having the formula $(R^{11})_3SiCR^{17}CR^{17}Si(R^{11})_3$ such as but not limited to Me$_3$SiCHCH$_2$, Me$_3$SiCHCHSiMe$_3$, (MeO)$_3$SiCHCH$_2$, or (EtO)$_3$SiCHCH$_2$. In a still further embodiment, ligand L in formula (I) or (II) may be a allene such as but not limited to CH$_2$CCCH$_2$ or Me$_2$CCCMe$_2$. In another embodiment, ligand L in formula (I) or (II) may be an alkylisocyanide such as but not limited to Me$_3$CNC. In a further embodiment, ligand L in formula (I) or (II) may be an allylsilane having the formula $(R^{15})_3SiC(R^{17})_2CR^{17}C(R^{17})_2$ such as but not limited to (MeO)$_3$SiCH$_2$CHCH$_2$, (i-Pr)$_3$SiCH$_2$CHCH$_2$ and Me$_3$SiCH$_2$CHCH$_2$. In the aforementioned formulas and throughout the specification, the term "Me" indicates a methyl group, "Et" indicates an ethyl group, and "i-Pr" indicates an isopropyl group.

In the above formulas (I) and (II), the organometallic bond between the metal atom (M) and ligand (L) is either 2 single bonds or 1 single bond. In certain embodiments, the bond energy between at least one of the metal atoms to L, metal atom to 0, and/or metal atom to N may be weaker than the bond energies found in the balance of the complex. It is believed that this may allow, in certain instances and under certain process conditions, for the complex to be readily dissociated at these particular bonds into its constituent components.

In one embodiment, the metal complexes described herein may be synthesized by reacting an amine with a β-diketone compound to form a β-ketoimine intermediate product. The amine may be, for example, a primary amine having the formula H$_2$NR$^4$ wherein R$^4$ can be any one of the groups or atoms described above. Non-limiting examples of a primary amine having the aforementioned formula include methyl amine, ethyl amine, propyl amine, and isopropyl amine. The β-diketone may be a compound having the formula R$^1$C(O)CHR$^2$C(O)R$^3$ wherein R$^1$, R$^2$, and R$^3$ can each independently be anyone of the groups or atoms described above. A non-limiting example of a β-diketone compound having the aforementioned formula is 2,4-pentanedione, 1,1,1-triflouro-2,4-pentane dione, 2,4-hexanedione, and 3,5-heptanedione.

The reaction of the amine with the β-diketone compound may be conducted in the presence of a solvent. Suitable solvents include, but are not limited to, ethers (e.g. diethylether (Et$_2$O), tetrahydrofuran ("THF"), di-n-butyl ether, 1,4-dioxane, or ethylene glycol dimethyl ether); nitriles (e.g. CH$_3$CN); or aromatic compounds (e.g. toluene), alone or in admixture thereof. In certain embodiments, the solvent is THF. The reaction temperature may range from −78° C. to the boiling point of the solvent. The reaction time may range from about 0 hours or instantaneous to about 48 hours, or from about 4 to about 12 hours. In certain embodiments, the intermediate product may be purified by standard procedures such as distillation, chromatography, recrystallization, and/or trituration. In some instances, however, the reaction of the amine with the β-diketone compound may be conducted in the absence of a solvent, particularly if the resulting β-ketoimine intermediate product is a liquid.

In certain embodiments, the β-ketoimine intermediate product may be one or more of the following three tautomeric isomers having the following formulas (III), (IV), or (V):

In the above formulas, variables $R^1$, $R^2$, $R^3$, and $R^4$ can each independently be any of the atoms or groups described herein.

In certain embodiments, the β-diketone compound may need to be activated prior to its reaction with the amine. In these embodiments, the β-diketone compound can be activated, for example, by a silylation or a halogenation process.

In one particular embodiment, a metal complex having the formula (I) described herein wherein M is Cu may be prepared by deprotonating (i.e., removing the acidic proton) the β-ketoimine intermediate product from the reaction of the amine with the β-diketone compound using one or more bases and then chelating to Cu(I) in the presence of the stabilizing ligand (L). A non-limiting example of this reaction is illustrated in the following equation (4):

In Equation (4), the β-ketoimine intermediate product, which is a compound of formula (V), is reacted in the presence of a base which is n-butyllithium, a copper (I) source which is copper chloride and a stabilizing ligand (L) which is any one of ligand (L) described herein to form the Cu(I) complex as shown above and lithium chloride. Other bases that could be used in the above reaction include, but are not limited to, lithium hydride, sodium hydride, potassium hydride, sodium bis(trimethylsilylamide), lithium diisopropylamide, potassium t-butoxide, etc. Other sources of copper(I) that could be used in above reaction include, but are not limited to, copper(I) bromide, copper(I) iodide, copper(I) trifluoroacetate, copper(I) trifluoromethylsulfonate benxene adduct, copper(I)alkoxide, copper(I) amide, copper(I) acetate, copper(I) phenoxide, copper(I) acetamide, and copper(I) alkoxide. In embodiments where other metal or mixed metal complexes are prepared, the metal source is one or more metal salts containing the desired metal M. The anticipated yield of the metal or Cu(I) complex may range from about 5% to about 95% of the theoretical yield. In certain embodiments, the final product, or metal complex, may be purified by standard procedures such as distillation, sublimation, chromatography, recrystallization, and/or trituration.

In certain embodiments where M is copper, a copper complex can be prepared by first synthesizing their analogous copper (II) bis(ketoimine) complexes then reacting them with a copper metal in the presence of stabilizing ligand L.

In alternative embodiments where M is copper, the β-ketoimine intermediate product can be reacted directly with a copper(I) aryl such as copper mesitylene to form the Cu(I) complex having the formula (I). In still further embodiments, the Cu(I) complexes can be prepared from its constituent parts, i.e., the β-ketoimine intermediate product, stabilizing ligand (L), and Cu(I) atom, in a suitable electrochemical process.

As mentioned previously, the metal complexes described herein may be used as precursors for the deposition of a metal, metal-containing, or alloy thereof film onto a substrate. Examples of suitable substrates include but are not limited to, semiconductor materials such as gallium arsenide ("GaAs"), boronitride ("BN") silicon, and compositions containing silicon such as crystalline silicon, polysilicon, amorphous silicon, epitaxial silicon, silicon dioxide ("SiO₂"), silicon carbide ("SiC"), silicon oxycarbide ("SiOC"), silicon nitride ("SiN"), silicon carbonitride ("SiCN"), organosilicate glasses ("OSG"), organofluorosilicate glasses ("OFSG"), fluorosilicate glasses ("FSG"), and other appropriate substrates or mixtures thereof. Substrates may further comprise a variety of layers to which the film is applied thereto such as, for example, antireflective coatings, photoresists, organic polymers, porous organic and inorganic materials, metals such as copper and aluminum, or diffusion barrier layers. The metal complexes may be deposited using any of the techniques described herein or known in the art. Exemplary deposition techniques include, but are not limited to, chemical vapor deposition (CVD), atomic layer deposition (ALD), plasma-assisted chemical vapor deposition (PACVD), and plasma-enhanced chemical vapor deposition (PECVD).

In certain embodiments, the metal complexes are deposited onto a substrate using a CVD or ALD technique. The deposition of the metal complexes may be conducted at temperatures of 400° C. or below, or 200° C. or below, or 100° C. or below. In a typical CVD deposition process, the metal complex is introduced into a reaction chamber such as a vacuum chamber. In certain embodiments, other chemical reagents, besides the metal complex, may be introduced before, during, and/or after the introduction of the metal complex. An energy source, such as, for example, thermal, plasma or other source, energizes the metal complex and optional chemical reagents thereby forming a film on at least a portion of the substrate.

As mentioned previously, in certain embodiments, a chemical reagent may be introduced before, during, and/or after the introduction of the metal complex into the reaction chamber. The choice of chemical reagent may depend upon the composition of the desired resultant films. For example, in one embodiment, reaction with a halogen-containing chemical reagent may form a film of metal halide, whereas in another embodiment, reaction with an oxidant chemical reagent will yield a metal oxide film. Exemplary chemical reagents include, but are not limited to oxidants (i.e., $O_2$, NO, $NO_2$, $O_3$, CO, $CO_2$, etc.); water; halides; halogen-containing silanes; alkylchlorosilanes, alkylbromosilanes, or alkyliodosilanes; silicon halide complexes such as silicon tetrachloride, silicon tetrabromide, or silicon tetraiodide; halogenated tin complexes such as alkylchlorostannanes, alkylbromostannanes, or alkyliodostannanes; germane complexes such as alkylchlorogermanes, alkylbromogermanes, or alkyliodiogermanes; boron trihalide complexes such as borontrichloride, boron tribromide, or boron triodide; aluminum halide complexes such as aluminum chloride, aluminum bromide, or aluminum iodide; alkylaluminum halides; gallium halide complexes such as gallium trichloride, gallium tribromide, or gallium triodide; or combinations thereof. It is also envisioned that derivatives of the above complexes may also be used. The chemical reagents may be delivered directly as a gas to the reaction chamber, delivered as a vaporized liquid, a sublimed solid and/or transported by an inert carrier gas into the reaction chamber. Examples of inert carrier gases include nitrogen, hydrogen, argon, xenon, etc.

In certain embodiments, the metal film such as where M is Cu as shown below may form on the substrate surface by a disproportionation reaction such as that depicted in Equation 5 below.

In another embodiment, a film comprising any one of the metals described herein may be deposited onto the surface of a substrate in the presence of a reducing agent to, for example, reduce the film to desired metal. A metal complex having the formula (I) or (II) may be introduced into a CVD or ALD reactor along with a reducing agent. The reducing agent is typically introduced in gaseous form. Examples of suitable reducing agents include, but are not limited to, alcohols, hydrogen gas, hydrogen plasma, remote hydrogen plasma, silanes (i.e., diethylsilane, ethylsilane, dimethylsilane, phenylsilane, silane, disilane, aminosilanes), boranes (i.e., borane, diborane), alanes, germanes, hydrazines, ammonia, or mixtures thereof.

In certain embodiments, a metal film is deposited from the complexes having formula (I) or (II) via an ALD deposition process. During a typical ALD process, one or more gaseous or vaporized precursors are introduced into the process chamber which houses the substrate in alternating pulses within a process cycle. Preferably, each process cycle forms no more than about one monolayer of material by adsorption and preferably by chemisorption. The number of process cycles used to grow the layer depends on the thickness desired but may generally exceed 1,000 cycles. For semiconductor devices, the process cycle is repeated until the barrier or seed layer within the dual damascene structure has a thickness sufficient to perform its desired function.

During ALD processing, the substrate is kept at a temperature range that facilitates chemisorption, i.e., is low enough to maintain intact bonds between adsorbed species and the underlying substrate yet high enough to avoid condensation of the precursors and to provide sufficient activation energy for the desired surface reactions in each process cycle. The process chamber temperature may range from 0° C. to 400° C., or from 0° C. to 300° C., or from 0° C. to 2750° C. The pressure within the process chamber during ALD processing may range from 0.1 to 1000 Torr, of from 0.1 to 15 Torr, or from 0.1 to 10 Torr. It is understood, however, that the temperature and pressure for any particular ALD process may vary depending upon the one or more precursors involved.

Any of the aforementioned film formation methods described herein, as well as other film formation methods known in the art, may be used alone or in combination. For example, in one embodiment, a mixed composition copper-containing film may be formed by sequentially depositing a copper oxide film followed by a copper metal film and then reducing the multilayers to provide a pure copper film.

In certain embodiments, the metal complex described herein may be dissolved in a suitable solvent such as an amine (e.g., triethylamine), an ether (e.g., THF), an aromatic (e.g., toluene) or any other solvent disclosed herein, to form a solution. The resulting solution may be flash vaporized in a Direct Liquid Injection (DLI) system for vapor delivery into an ALD or CVD reaction chamber. In other embodiments, the complexes described herein can be dissolved in a stabilizing liquid such as olefins or alkynes prior to introduction to a DLI system.

EXAMPLES

In the following examples, EDX analysis was performed on a Hitachi S-750 Scanning Electron Microscope. The G.C.M.S. Spectra for the examples were performed on a Hewlett Packard 5890 Series 11 G.C. and 5972 series mass selective detector with a HP-5MS. The nuclear NMR analyses for the examples were obtained on a Bruker AMX 500 spectrometer operating at 500.MHz ($^1$H). Chemical shifts were set from $C_6D_6$ at 7.16 ppm in $^1$H and 128.39 parts per million (ppm) in $^{13}$C. X-ray analysis was conducted on a Bruker D8 platform diffractometer equipped with an APEX CCD detector and a Kryoflex cryostat.

Example 1

Synthesis of β-ketoimine Intermediate Product Where $R^1$, $R^3$, and $R^4$ are Methyl Groups and $R^2$ is Hydrogen Equimolar amounts of 2,4-pentanedione and methylamine were mixed to provide an approximately 1 molar mixture in the solvent tetrahydrofuran (THF) and stirred overnight to provide a solution. The solution was allowed to stand overnight over excess anhydrous sodium sulfate. The next day, the solution was decanted from the sodium sulfate and dried over 3A molecular sieves. The following day, the remaining THF was stripped from the solution under vacuum and the resulting solid was sublimed at 50° C. The final product, a white crystalline solid, was collected and stored under nitrogen. Purity by G.C.M.S. was found to be greater than 98%.

Example 2

Synthesis of Cu(I)(MeC(O)CHC(NMe)Me)(trimethylvinylsilane) Complex

Under a nitrogen atmosphere, a first solution was prepared by dissolving 2.26 grams (0.022 moles) of the β-ketoimine intermediate product, prepared in accordance with the method described in Example 1, in approximately 100 milliliters (ml) of dry hexane which was then cooled to 0° C. After the solution reached 0° C., 8 ml of a 2.5M concentration n-butyl lithium (0.02 moles) was gradually added to the first solution over a period of 10 minutes. The first solution was stirred for 60 minutes at 0° C. and then allowed to warm to room temperature upon which it was stirred for another 2 hours. In a separate vessel, a second mixture was prepared containing 2.0 g (0.02 moles) of copper chloride and 20 ml of dry hexane containing 2.2 g (0.22 moles) of trimethylvinylsilane which was cooled to 0° C. under a nitrogen atmosphere. The first solution was then added dropwise over 30 minutes to the second mixture and then the mixture was allowed to stir overnight.

Figure 1:
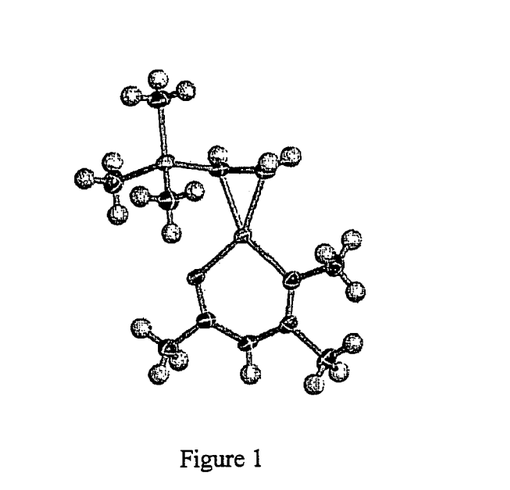
FIG. 1 provides an exemplary structure of one of the complexes comprising copper described herein or Cu(I)(MeC(O)CHC(NMe)Me)(trimethylvinylsilane).

The next day, the mixture was filtered under a nitrogen atmosphere and the hexane solvent was stripped off under vacuum to provide a solid crude product. This solid crude product was sublimed at a temperature of 30° C., pressure of 20 mTorr, and cold finger at 8° C. to provide 2.62 g of the desired copper complex as a yellow crystalline solid, yield 47%, and melting point ranging from 36–37° C. The NMR results for the copper complex product were as follows: $^1$H NMR (500 MHz, $C_6D_6$): δ=0.24 (s, 9H), δ=1.57 (s, 3H), δ=2.09 (s, 3H), δ=2.85 (s, 3H), δ=3.6 (d, 1H), δ=3.76 (d, 1H), δ=3.96 (dd, 1H). $^{13}$C NMR (500M Hz, $C_6D_6$): δ=0.2 (s, 1C), δ=21.5 (s, 1C), δ=27.9 (s, 1C), δ=42.7 (s, 1C), δ=77.5 (s, 1C), δ=86.3 (s, 1C), δ=97.7 (s, 1C). δ=170.1 (s, 1C), δ=180.7 (s, 1C). The structure of the product, or the Cu(I)(MeC(O)CHC(NMe)Me)(trimethylvinylsilane) complex, is provided in FIG. 1 and was obtained by X-ray diffraction of a single crystal grown by sublimation at room temperature.

Example 3

CVD Deposition Using Cu(I)(MeC(O)CHC(NMe)Me)(trimethylvinylsilane)

Figure 2:
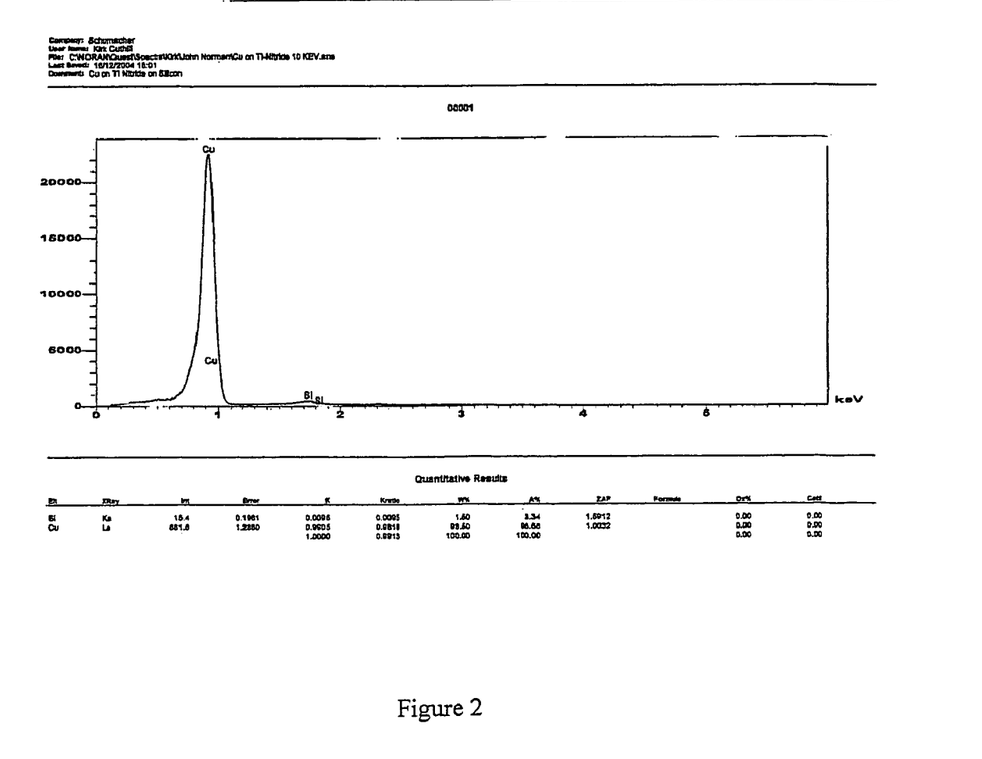
FIG. 2 provides the results of EDX analysis of a film deposited via CVD deposition using Cu(I)(MeC(O)CHC(NMe)Me)(trimethylvinylsilane).

A 3 cm×1 cm silicon wafer coated with a 200 Angstrom thick diffusion layer of TiN was placed into the chamber of a miniature CVD reactor such as that depicted in FIG. 1 of U.S. Pat. No. 5,098,516. The wafer was heated to a temperature of 165° C. under vacuum at 35 mTorr. Vapor from a 100 mg sample of the Cu(I)(MeC(O)CHC(NMe)Me)(trimethylvinylsilane) precursor was introduced into the reactor and contacted the heated substrate surface. The precursor vapor was flowed for a total of 50 minutes during which time a copper colored film was observed to grow upon the titanium nitride surface. The precursor flow was then ceased and heat and vacuum turned off. The substrate having the film deposited thereupon was removed once it had cooled to room temperature. EDX analysis of the film showed that the film was comprised of copper with no detectable carbon, as shown in FIG. 2.

Example 4

Demonstration of Disproportionation Reaction and Volatility of $Cu(II)(MeC(O)CHC(NMe)Me)_2$ by-product

The present example demonstrates that the deposition reaction proceeds by a disproportionation reaction. An approximately 2.0 microliter, 2.0 M solution in THF of the sublimed Cu(I)(MeC(O)CHC(NMe)Me)(trimethylvinylsilane) complex which was prepared in accordance with Example 2 was injected into a Gas Chromatography/Mass Spectrometer. In this system, the injected sample is first flash vaporized on a heated stage of about 150 to 200° C. and the resulting vapors fed into a capillary gas chromatography column where it is separated into its constituent components which are then identified by a Mass Spectrometer. The resulting vapors fed into the capillary gas chromatography column were observed to be trimethylvinylsilane and $Cu(II)(MeC(O)CHC(NMe)Me)_2$ indicating that a disproportionation reaction has occurred upon the heated stage.

Figure 3:
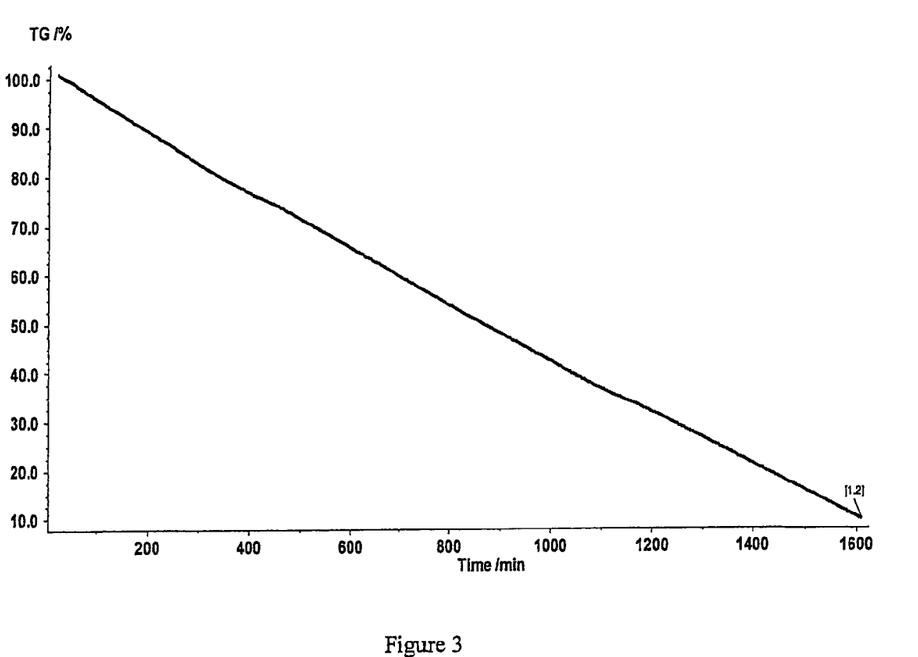
FIG. 3 shows the weight loss over time of the Cu(II)(MeC(O)CHC(NMe)Me)$_2$ by-product of the disproportionation reaction that was heated at 100° C. under a flowing stream of dry nitrogen at ambient pressure.

To demonstrate the volatility of the Cu(II)(MeC(O)CHC(NMe)Me)$_2$ by-product of the CVD disproportionation reaction, a sample of the byproduct, which was prepared by the disproportionation reaction of the Cu(I)(MeC(O)CHC(NMe)Me)(trimethylvinylsilane) complex, is loaded into a microbalance and heated at 100° C. in a steadily flowing stream of dry nitrogen. The steady and even weight loss of the sample, shown in FIG. 3 below, indicates the volatility of this species.

We claim:

1. A complex represented by formula (I) or (II):

wherein M is a metal selected from Cu, Au, Ag, Co, Ru, Rh, Pt, In, Pd, Ni, Os, and mixtures thereof;

wherein $R^1$, $R^2$, $R^3$, and $R^4$ are each independently a hydrogen atom; an alkyl having a formula $C_nH_{2n+1}$ wherein n is a number ranging from 1 to 20; a fluoroalkyl having a formula $C_nH_xF_y$ wherein the product of (x+y) equals the product of (2n+1) and n is a number ranging from 1 to 20; an alkylsilane having a formula $(R^5)_3Si$ wherein $R^5$ is each independently an alkyl, a fluoralkyl, an amide, or an alkoxy comprising from 1 to 20 carbon atoms; an aryl comprising from 6 to 18 carbon atoms; an alkyl-substituted aryl comprising from 6 to 18 carbon atoms; a fluoroalkyl-substituted aryl comprising from 6 to 18 carbon atoms; a fluoroaryl comprising from 6 to 18 carbon atoms; an alkyl-substituted fluoroaryl comprising from 6 to 18 carbon atoms; a fluoroalkyl-substituted fluoroaryl comprising from 6 to 18 carbon atoms; an ether having a formula $(CH_2)_nO(C_mH_{2m+1})$ where n is a number ranging from 1 to 20 and m is a number ranging from 1 to 20; an alkoxy comprising from 1 to 20 carbon atoms; an amide group comprising from 1 to 20 carbon atoms; a halogen atom; and a nitro group $NO_2$;

wherein L is a ligand selected from carbon monoxide; an alkylnitrile comprising from 2 to 20 carbon atoms; a silylnitrile having a formula $(R^6)_3SiCN$ wherein $R^6$ is each independently an alkyl comprising from 1 to 20 carbon atoms; an alkyne comprising from 1 to 20 carbon atoms; a silylalkyne having a formula $(R^7)_3SiCCR^8$ wherein $R^7$ is each independently an alkyl, an amide, or an alkoxy comprising from 1 to 20 carbon atoms and $R^8$ is each independently a hydrogen atom, an alkoxy, or an alkyl comprising from 1 to 20 carbon atoms; a bis(silyl)alkyne having a formula $(R^9)_3SiCCSi(R^9)_3$ wherein $R^9$ is each independently an alkyl, an amide or an alkoxy comprising from 1 to 20 carbon atoms; an alkene comprising from 1 to 20 carbon atoms; a diene comprising from 1 to 20 carbon atoms; a triene comprising from 1 to 20 carbon atoms; a silylalkene having a formula $(R^{10})_3SiC(R^{17})C(R^{17})_2$ wherein $R^{10}$ is each independently an alkyl, an alkoxy, or an amide comprising from 1 to 20 carbon atoms and $R^{17}$ is independently a hydrogen atom or an alkyl group comprising from 1 to 20 carbon atoms; a bis(silyl)alkene having a formula $(R^{11})_3SiCR^{17}CR^{17}Si(R^{11})_3$ wherein $R^{11}$ is each independently an alkyl comprising from 1 to 20 carbon atoms, an alkoxy, or an amide comprising from 1 to 20 carbon atoms and $R^{17}$ is independently a hydrogen atom or an alkyl group comprising from 1 to 20 carbon atoms; an allene comprising from 3 to 20 carbon atoms; a allene having a formula $(R^{12})_2CCC(R^{12})_2$ where $R^{12}$ is each independently a hydrogen atom, an alkyl, an alkyl silane, an alkoxysilane, or an amidosilane having a formula $(R^{13})_3Si$ wherein $R^{13}$ is each independently an alkyl, alkoxy, or an amide comprising from 1 to 20 carbon atoms; an alkylisocyanide comprising from 1 to 20 carbon atoms; a silylisocyanide having a formula $(R^{14})_3SiNC$ wherein $R^{14}$ is each independently an alkyl comprising from 1 to 20 carbon atoms; an allyl comprising from 1 to 20 carbon atoms; an allylsilane having a formula $(R^{15})_3SiC(R^{17})_2R^{17}C(R^{17})_2$ where $R^{15}$ is an alkyl, an alkoxy, or an amide comprising from 1 to 20 carbon atoms and $R^{17}$ is independently a hydrogen atom or an alkyl group having from 1 to 20 carbon atoms; and a bis(silyl)allyl having a formula $(R^{16})_3SiC(R^{17})_2CR^{17}CR^{17}Si(R^{16})_3$ where $R^{16}$ comprises from 1 to 20 carbon atoms and $R^{17}$ is independently a hydrogen atom or an alkyl group having from 1 to 20 carbon atoms; and wherein an organometallic bond between M and L is selected from 2 single bonds and 1 single bond.

2. The complex of claim 1 wherein M is Cu.

3. The complex of claim 1 wherein at least one of substituents $R^1$ and $R^2$, $R^2$ and $R^3$, and $R^3$ and $R^4$ connect to form a cyclic structure.

4. The complex of claim 3 wherein substituents $R^3$ and $R^4$ connect to form a cyclic structure.

5. The complex of claim 3 wherein substituents $R^1$ and $R^2$ connect to form a cyclic structure.

6. The complex of claim 1 having formula (I).

7. The complex of claim 1 having formula (II).

8. The complex of claim 7 wherein the two M atoms are the same.

9. The complex of claim 7 wherein the two M atoms are different.

10. A method for depositing a film comprising metal on a substrate, the method comprising:

contacting the substrate with a metal complex having formula (I) or (II) wherein the contacting is conducted at conditions sufficient for the complex to react and form the film (I)

(II)

wherein M is a metal selected from Cu, Au, Ag, Co, Ru, Rh, Pt, In, Pd, Ni, Os, and mixtures thereof;

wherein $R^1$, $R^2$, $R^3$, and $R^4$ are each independently a hydrogen atom; an alkyl having a formula $C_nH_{2n+1}$ wherein n is a number ranging from 1 to 20; a fluoroalkyl having a formula $C_nH_xF_y$ wherein the product of (x+y) equals the product of (2n+1) and n is a number ranging from 1 to 20; an alkylsilane having a formula $(R^5)_3Si$ wherein $R^5$ is each independently an alkyl, a fluoralkyl, an amide, or an alkoxy comprising from 1 to 20 carbon atoms; an aryl comprising from 6 to 18 carbon atoms; an alkyl-substituted aryl comprising from 6 to 18 carbon atoms; a fluoroalky-substituted aryl comprising from 6 to 18 carbon atoms; a fluoroaryl comprising from 6 to 18 carbon atoms; an alkyl-substituted fluoroaryl comprising from 6 to 18 carbon atoms; a fluoroalkyl-substituted fluoroaryl comprising from 6 to 18 carbon atoms; an ether having a formula $(CH_2)_nO(C_mH_{2m+1})$ where n is a number ranging from 1 to 20 and m is a number ranging from 1 to 20; an alkoxy comprising from 1 to 20 carbon atoms; an amide group comprising from 1 to 20 carbon atoms; a halogen atom; and a nitro group $NO_2$;

wherein L is a ligand selected from carbon monoxide; an alkylnitrile comprising from 2 to 20 carbon atoms; a silylnitrile having a formula $(R^6)_3SiCN$ wherein $R^6$ is each independently an alkyl comprising from 1 to 20 carbon atoms; an alkyne comprising from 1 to 20 carbon atoms; a silylalkyne having a formula $(R^7)_3SiCCR^8$ wherein $R^7$ is each independently an alkyl, an amide, or an alkoxy comprising from 1 to 20 carbon atoms and $R^8$ is each independently a hydrogen atom, an alkoxy, or an alkyl comprising from 1 to 20 carbon atoms; a bis(silyl)alkyne having a formula $(R^9)_3SiCCSi(R^9)_3$ wherein $R^9$ is each independently an alkyl, an amide or an alkoxy comprising from 1 to 20 carbon atoms; an alkene comprising from 1 to 20 carbon atoms; a diene comprising from 1 to 20 carbon atoms; a triene comprising from 1 to 20 carbon atoms; a silylalkene having a formula $(R^{10})_3SiC(R^{17})C(R^{17})_2$ wherein $R^{10}$ is each independently an alkyl, an alkoxy, or an amide comprising from 1 to 20 carbon atoms and $R^{17}$ is independently a hydrogen atom or an alkyl group comprising from 1 to 20 carbon atoms; a bis(silyl) alkene having a formula $(R^{11})_3SiCR^{17}CR^{17}Si(R^{11})_3$ wherein $R^{11}$ is each independently an alkyl comprising from 1 to 20 carbon atoms, an alkoxy, or an amide comprising from 1 to 20 carbon atoms and $R^{17}$ is independently a hydrogen atom or an alkyl group comprising from 1 to 20 carbon atoms; an allene comprising from 3 to 20 carbon atoms; a allene having a formula $(R^{12})_2CCC(R^{12})_2$ where $R^{12}$ is each independently a hydrogen atom, an alkyl, an alkyl silane, an alkoxysilane, or an amidosilane having a formula $(R^{13})_3Si$ wherein $R^{13}$ is each independently an alkyl, alkoxy, or an amide comprising from 1 to 20 carbon atoms; an alkylisocyanide comprising from 1 to 20 carbon atoms; a silylisocyanide having a formula $(R^{14})_3SiNC$ wherein $R^{14}$ is each independently an alkyl comprising from 1 to 20 carbon atoms; an allyl comprising from 1 to 20 carbon atoms; an allylsilane having a formula $(R_{15})_3SiC(R^{17})_2R^{17}C(R^{17})_2$ where $R^{15}$ is an alkyl, an alkoxy, or an amide comprising from 1 to 20 carbon atoms and $R^{17}$ is independently a hydrogen atom or an alkyl group having from 1 to 20 carbon atoms; and a bis(silyl)allyl having a formula $(R^{16})_3SiC(R^{17})_2CR^{17}CR^{17}Si(R^{16})_3$ where $R^{16}$ comprises from 1 to 20 carbon atoms and $R^{17}$ is independently a hydrogen atom or an alkyl group having from 1 to 20 carbon atoms; and wherein an organometallic bond between M and L is selected from 2 single bonds and 1 single bond.

11. An electronic device comprising a film comprising metal wherein the film is deposited from a precursor mixture comprising at least one complex having formula (I) or (II):

(I)

(II)

wherein M is a metal selected from Cu, Au, Ag, Co, Ru, Rh, Pt, In, Pd, Ni, Os, and mixtures thereof;

wherein $R^1$, $R^2$, $R^3$, and $R^4$ are each independently a hydrogen atom; an alkyl having a formula $C_nH_{2n+1}$ wherein n is a number ranging from 1 to 20; a fluoroalkyl having a formula $C_nH_xF_y$ wherein the product of (x+y) equals the product of (2n+1) and n is a number ranging from 1 to 20; an alkylsilane having a formula $(R^5)_3Si$ wherein $R^5$ is each independently an alkyl, a fluoralkyl, an amide, or an alkoxy comprising from 1 to 20 carbon atoms; an aryl comprising from 6 to 18 carbon atoms; an alkyl-substituted aryl comprising from 6 to 18 carbon atoms; a fluoroalky-substituted aryl comprising from 6 to 18 carbon atoms; a fluoroaryl comprising from 6 to 18 carbon atoms; an alkyl-substituted fluoroaryl comprising from 6 to 18 carbon atoms; a fluoroalkyl-substituted fluoroaryl comprising from 6 to 18 carbon atoms; an ether having a formula $(CH_2)_nO(C_mH_{2m+1})$ where n is a number ranging from 1 to 20 and m is a number ranging from 1 to 20; an alkoxy comprising from 1 to 20 carbon atoms; an amide group comprising from 1 to 20 carbon atoms; a halogen atom; and a nitro group $NO_2$;

wherein L is a ligand selected from carbon monoxide; an alkylnitrile comprising from 2 to 20 carbon atoms; a silylnitrile having a formula $(R^6)_3SiCN$ wherein $R^6$ is each independently an alkyl comprising from 1 to 20 carbon atoms; an alkyne comprising from 1 to 20 carbon atoms; a silylalkyne having a formula $(R^7)_3SiCCR^8$ wherein $R^7$ is each independently an alkyl, an amide, or an alkoxy comprising from 1 to 20 carbon atoms and $R^8$ is each independently a hydrogen atom, an alkoxy, or an alkyl comprising from 1 to 20 carbon atoms; a bis(silyl)alkyne having a formula $(R^9)_3SiCCSi(R^9)_3$ wherein $R^9$ is each independently an alkyl, an amide or an alkoxy comprising from 1 to 20 carbon atoms; an alkene comprising from 1 to 20 carbon atoms; a diene comprising from 1 to 20 carbon atoms; a triene comprising from 1 to 20 carbon atoms; a silylalkene having a formula $(R^{10})_3SiC(R^{17})C(R^{17})_2$ wherein $R^{10}$ is each independently an alkyl, an alkoxy, or an amide comprising from 1 to 20 carbon atoms and $R^{17}$ is independently a hydrogen atom or an alkyl group comprising from 1 to 20 carbon atoms; a bis(silyl) alkene having a formula $(R^{11})_3SiCR^{17}CR^{17}Si(R^{11})_3$ wherein $R^{11}$ is each independently an alkyl comprising from 1 to 20 carbon atoms, an alkoxy, or an amide comprising from 1 to 20 carbon atoms and $R^{17}$ is independently a hydrogen atom or an alkyl group comprising from 1 to 20 carbon atoms; an allene comprising from 3 to 20 carbon atoms; an allene having a formula $(R^{12})_2CCC(R^{12})_2$ where $R^{12}$ is each independently a hydrogen atom, an alkyl, an alkyl silane, an alkoxysilane, or an amidosilane having a formula $(R^{13})_3Si$ wherein $R^{13}$ is each independently an alkyl, alkoxy, or an amide comprising from 1 to 20 carbon atoms; an alkylisocyanide comprising from 1 to 20 carbon atoms; a silylisocyanide having a formula $(R^{14})_3SiNC$ wherein $R^{14}$ is each independently an alkyl comprising from 1 to 20 carbon atoms; an allyl comprising from 1 to 20 carbon atoms; an allylsilane having a formula $(R^{15})_3SiC(R^{17})_2R^{17}C(R^{17})_2$ where $R^{15}$ is an alkyl, an alkoxy, or an amide comprising from 1 to 20 carbon atoms and $R^{17}$ is independently a hydrogen atom or an alkyl group having from 1 to 20 carbon atoms; and a bis(silyl)allyl having a formula $(R^{16})_3SiC(R^{17})_2CR^{17}CR^{17}Si(R^{16})_3$ where $R^{16}$ comprises from 1 to 20 carbon atoms and $R^{17}$ is independently a hydrogen atom or an alkyl group having from 1 to 20 carbon atoms; and wherein an organometallic bond between the M and L is selected from 2 single bonds and 1 single bond.

12. A method of making a metal complex having a formula (I) or (II):

wherein M is a metal selected from Cu, Au, Ag, Co, Ru, Rh, Pt, In, Pd, Ni, Os, and mixtures thereof;

wherein $R^1$, $R^2$, $R^3$, and $R^4$ are each independently a hydrogen atom; an alkyl having a formula $C_nH_{2n+1}$ wherein n is a number ranging from 1 to 20; a fluoroalkyl having a formula $C_nH_xF_y$, wherein the product of (x+y) equals the product of (2n+1) and n is a number ranging from 1 to 20; an alkylsilane having a formula $(R^5)_3Si$ wherein $R^5$ is each independently an alkyl, a fluoroalkyl, an amide, or an alkoxy comprising from 1 to 20 carbon atoms; an aryl comprising from 6 to 18 carbon atoms; an alkyl-substituted aryl comprising from 6 to 18 carbon atoms; a fluoroalky-substituted aryl comprising from 6 to 18 carbon atoms; a fluoroaryl comprising from 6 to 18 carbon atoms; an alkyl-substituted fluoroaryl comprising from 6 to 18 carbon atoms; a fluoroalkyl-substituted fluoroaryl comprising from 6 to 18 carbon atoms; an ether having a formula $(CH_2)_nO(C_mH_{2m+1})$ where n is a number ranging from 1 to 20 and m is a number ranging from 1 to 20; an alkoxy comprising from 1 to 20 carbon atoms; an amide group comprising from 1 to 20 carbon atoms; a halogen atom; and a nitro group $NO_2$;

wherein L is a ligand selected from carbon monoxide; an alkylnitrile comprising from 2 to 20 carbon atoms; a silylnitrile having a formula $(R^6)_3SiCN$ wherein $R^6$ is each independently an alkyl comprising from 1 to 20 carbon atoms; an alkyne comprising from 1 to 20 carbon atoms; a silylalkyne having a formula $(R^7)_3SiCCR^8$ wherein $R^7$ is each independently an alkyl, an amide, or an alkoxy comprising from 1 to 20 carbon atoms and $R^8$ is each independently a hydrogen atom, an alkoxy, or an alkyl comprising from 1 to 20 carbon atoms; a bis(silyl)alkyne having a formula $(R^9)_3SiCCSi(R^9)_3$ wherein $R^9$ is each independently an alkyl, an amide or an alkoxy comprising from 1 to 20 carbon atoms; an alkene comprising from 1 to 20 carbon atoms; a diene comprising from 1 to 20 carbon atoms; a triene comprising from 1 to 20 carbon atoms; a silylalkene having a formula $(R^{10})_3SiC(R^{17})C(R^{17})_2$ wherein $R^{10}$ is each independently an alkyl, an alkoxy, or an amide comprising from 1 to 20 carbon atoms and $R^{17}$ is independently a hydrogen atom or an alkyl group comprising from 1 to 20 carbon atoms; a bis(silyl)alkene having a formula $(R^{11})_3SiCR^{17}CR^{17}Si(R^{11})_3$ wherein $R^{11}$ is each independently an alkyl comprising from 1 to 20 carbon atoms, an alkoxy, or an amide comprising from 1 to 20 carbon atoms and $R^{17}$ is independently a hydrogen atom or an alkyl group comprising from 1 to 20 carbon atoms; an allene comprising from 3 to 20 carbon atoms; a allene having a formula $(R^{12})_2CCC(R^{12})_2$ where $R^{12}$ is each independently a hydrogen atom, an alkyl, an alkyl silane, an alkoxysilane, or an amidosilane having a formula $(R^{13})_3Si$ wherein $R^{13}$ is each independently an alkyl, alkoxy, or an amide comprising from 1 to 20 carbon atoms; an alkylisocyanide comprising from 1 to 20 carbon atoms; a silylisocyanide having a formula $(R^{14})_3SiNC$ wherein $R^{14}$ is each independently an alkyl comprising from 1 to 20 carbon atoms; an allyl comprising from 1 to 20 carbon atoms; an allylsilane having a formula $(R^{15})_3SiC(R^{17})_2R^{17}C(R^{17})_2$ where $R^{15}$ is an alkyl, an alkoxy, or an amide comprising from 1 to 20 carbon atoms and $R^{17}$ is independently a hydrogen atom or an alkyl group having from 1 to 20 carbon atoms; and a bis(silyl)allyl having a formula $(R^{16})_3SiC(R^{17})_2CR^{17}CR^{17}Si(R^{16})_3$ where $R^{16}$ comprises from 1 to 20 carbon atoms and $R^{17}$ is independently a hydrogen atom or an alkyl group having from 1 to 20 carbon atoms; and wherein an organometallic bond between M and L is selected from 2 single bonds and 1 single bond, the method comprising:

reacting a primary amine with a β-diketone compound to form a β-ketoimine intermediate product; and deprotonating the β-ketoimine intermediate product using a base in the presence of a metal source and ligand (L) to form the copper complex having the formula (I) or (II).

13. Cu(I)(MeC(O)CHC(NMe)Me)(trimethylvinylsilane).

14. A complex represented by a following formula:

wherein $R^1$, $R^2$, $R^3$, and $R^4$ are each independently a hydrogen atom; an alkyl having a formula $C_nH_{2n+1}$ wherein n is a number ranging from 1 to 20; a fluoroalkyl having a formula $C_nH_xF_y$, wherein the product of (x+y) equals the product of (2n+1) and n is a number ranging from 1 to 20; an alkylsilane having a formula $(R^5)_3Si$ wherein $R^5$ is each independently an alkyl, a fluoralkyl, an amide, or an alkoxy comprising from 1 to 20 carbon atoms; an aryl comprising from 6 to 18 carbon atoms; an alkyl-substituted aryl comprising from 6 to 18 carbon atoms; a fluoroalky-substituted aryl comprising from 6 to 18 carbon atoms; a fluoroaryl comprising from 6 to 18 carbon atoms; an alkyl-substituted fluoroaryl comprising from 6 to 18 carbon atoms; a fluoroalkyl-substituted fluoroaryl comprising from 6 to 18 carbon atoms; an ether having a formula $(CH_2)_nO(C_mH_{2m+1})$ where n is a number ranging from 1 to 20 and m is a number ranging from 1 to 20; an alkoxy comprising from 1 to 20 carbon atoms; an amide group comprising from 1 to 20 carbon atoms; a halogen atom; and a nitro group $NO_2$;

wherein L is a ligand selected from carbon monoxide; an alkylnitrile comprising from 2 to 20 carbon atoms; a silylnitrile having a formula $(R^6)_3SiCN$ wherein $R^6$ is each independently an alkyl comprising from 1 to 20 carbon atoms; an alkyne comprising from 1 to 20 carbon atoms; a silylalkyne having a formula $(R^7)_3SiCCR^8$ wherein $R^7$ is each independently an alkyl, an amide, or an alkoxy comprising from 1 to 20 carbon atoms and $R^8$ is each independently a hydrogen atom, an alkoxy, or an alkyl comprising from 1 to 20 carbon atoms; a bis(silyl)alkyne having a formula $(R_9)_3SiCCSi(R^9)_3$ wherein $R^9$ is each independently an alkyl, an amide or an alkoxy comprising from 1 to 20 carbon atoms; an alkene comprising from 1 to 20 carbon atoms; a diene comprising from 1 to 20 carbon atoms; a triene comprising from 1 to 20 carbon atoms; a silylalkene having a formula $(R^{10})_3SiC(R^{17})C(R^{17})_2$ wherein $R^{10}$ is each independently an alkyl, an alkoxy, or an amide comprising from 1 to 20 carbon atoms and $R^{17}$ is independently a hydrogen atom or an alkyl group comprising from 1 to 20 carbon atoms; a bis(silyl)alkene having a formula $(R^{11})_3SiCR^{17}CR^{17}Si(R^{11})_3$ wherein $R^{11}$ is each independently an alkyl comprising from 1 to 20 carbon atoms, an alkoxy, or an amide comprising from 1 to 20 carbon atoms and $R^{17}$ is independently a hydrogen atom or an alkyl group comprising from 1 to 20 carbon atoms; an allene comprising from 3 to 20 carbon atoms; an allene having a formula $(R^{12})_2CCC(R^{12})_2$ where $R^{12}$ is each independently a hydrogen atom, an alkyl, an alkyl silane, an alkoxysilane, or an amidosilane having a formula $(R^{13})_3Si$ wherein $R^{13}$ is each independently an alkyl, alkoxy, or an amide comprising from 1 to 20 carbon atoms; an alkylisocyanide comprising from 1 to 20 carbon atoms; a silylisocyanide having a formula $(R^{14})_3SiNC$ wherein $R^{14}$ is each independently an alkyl comprising from 1 to 20 carbon atoms; an allyl comprising from 1 to 20 carbon atoms; an allylsilane having a formula $(R_{15})_3SiC(R^{17})_2R^{17}C(R^{17})_2$ where $R^{15}$ is an alkyl, an alkoxy, or an amide comprising from 1 to 20 carbon atoms and $R^{17}$ is independently a hydrogen atom or an alkyl group having from 1 to 20 carbon atoms; and a bis(silyl)allyl having a formula $(R^{16})_3SiC(R^{17})_2CR^{17}CR^{17}Si(R^{16})_3$ where $R^{16}$ comprises from 1 to 20 carbon atoms and $R^{17}$ is independently a hydrogen atom or an alkyl group having from 1 to 20 carbon atoms; and wherein an organometallic bond between M and L is selected from 2 single bonds and 1 single bond.

15. A complex represented by a following formula:

wherein $R^1$, $R^2$, $R^3$, and $R^4$ are each independently a hydrogen atom; an alkyl having a formula $C_nH_{2n+1}$ wherein n is a number ranging from 1 to 20; a fluoroalkyl having a formula $C_nH_xF_y$ wherein the product of (x+y) equals the product of (2n+1) and n is a number ranging from 1 to 20; an alkylsilane having a formula $(R^5)_3Si$ wherein $R^5$ is each independently an alkyl, a fluoralkyl, an amide, or an alkoxy comprising from 1 to 20 carbon atoms; an aryl comprising from 6 to 18 carbon atoms; an alkyl-substituted aryl comprising from 6 to 18 carbon atoms; a fluoroalky-substituted aryl comprising from 6 to 18 carbon atoms; a fluoroaryl comprising from 6 to 18 carbon atoms; an alkyl-substituted fluoroaryl comprising from 6 to 18 carbon atoms; a fluoroalkyl-substituted fluoroaryl comprising from 6 to 18 carbon atoms; an ether having a formula $(CH_2)_nO(C_mH_{2m+1})$ where n is a number ranging from 1 to 20 and m is a number ranging from 1 to 20; an alkoxy comprising from 1 to 20 carbon atoms; an amide group comprising from 1 to 20 carbon atoms; a halogen atom; and a nitro group $NO_2$;

wherein L is a ligand selected from carbon monoxide; an alkylnitrile comprising from 2 to 20 carbon atoms; a silylnitrile having a formula $(R^6)_3SiCN$ wherein $R^6$ is each independently an alkyl comprising from 1 to 20 carbon atoms; an alkyne comprising from 1 to 20 carbon atoms; a silylalkyne having a formula $(R^7)_3SiCCR^8$ wherein $R^7$ is each independently an alkyl, an amide, or an alkoxy comprising from 1 to 20 carbon atoms and $R^8$ is each independently a hydrogen atom, an alkoxy, or an alkyl comprising from 1 to 20 carbon atoms; a bis(silyl)alkyne having a formula $(R_9)_3SiCCSi(R^9)_3$ wherein $R^9$ is each independently an alkyl, an amide or an alkoxy comprising from 1 to 20 carbon atoms; an alkene comprising from 1 to 20 carbon atoms; a diene comprising from 1 to 20 carbon atoms; a triene comprising from 1 to 20 carbon atoms; a silylalkene having a formula $(R^{10})_3SiC(R^{17})C(R^{17})_2$ wherein $R^{17}$ is each independently an alkyl, an alkoxy, or an amide comprising from 1 to 20 carbon atoms and $R^{17}$ is independently a hydrogen atom or an alkyl group comprising from 1 to 20 carbon atoms; a bis(silyl)alkene having a formula $(R^{11})_3SiCR^{17}CR^{17}Si(R^{11})_3$ wherein $R^{11}$ is each independently an alkyl comprising from 1 to 20 carbon atoms, an alkoxy, or an amide comprising from 1 to 20 carbon atoms and $R^{17}$ is independently a hydrogen atom or an alkyl group comprising from 1 to 20 carbon atoms; an allene comprising from 3 to 20 carbon atoms; a allene having a formula $(R^{12})_2CCC(R^{12})_2$ where $R^{12}$ is each independently a hydrogen atom, an alkyl, an alkyl silane, an alkoxysilane, or an amidosilane having a formula $(R^{13})_3Si$ wherein $R^{13}$ is each independently an alkyl, alkoxy, or an amide comprising from 1 to 20 carbon atoms; an alkylisocyanide comprising from 1 to 20 carbon atoms; a silylisocyanide having a formula $(R^{14})_3SiNC$ wherein $R^{14}$ is each independently an alkyl comprising from 1 to 20 carbon atoms; an allyl comprising from 1 to 20 carbon atoms; an allylsilane having a formula $(R^{15})_3SiC(R^{17})_2R^{17}C(R^{17})_2$ where $R^{15}$ is an alkyl, an alkoxy, or an amide comprising from 1 to 20 carbon atoms and $R^{17}$ is independently a hydrogen atom or an alkyl group having from 1 to 20 carbon atoms; and a bis(silyl)allyl having a formula $(R^{16})_3SiC(R^{17})_2CR^{17}CR^{17}Si(R^{16})_3$ where $R^{16}$ comprises from 1 to 20 carbon atoms and $R^{17}$ is independently a hydrogen atom or an alkyl group having from 1 to 20 carbon atoms; and wherein an organometallic bond between M and L is selected from 2 single bonds and 1 single bond.

* * * * *

UNITED STATES PATENT AND TRADEMARK OFFICE
CERTIFICATE OF CORRECTION

| | | |
|---|---|---|
| PATENT NO. | : 7,034,169 B1 | Page 1 of 1 |
| APPLICATION NO. | : 11/111455 | |
| DATED | : April 25, 2006 | |
| INVENTOR(S) | : John Anthony Thomas Norman | |

It is certified that error appears in the above-identified patent and that said Letters Patent is hereby corrected as shown below:

Column 22, line 48, delete "$R^{17}$" and insert --$R^{10}$--.

Signed and Sealed this

Fourth Day of July, 2006

JON W. DUDAS
*Director of the United States Patent and Trademark Office*